United States Patent [19]

Bock

[11] Patent Number: 4,874,707
[45] Date of Patent: Oct. 17, 1989

[54] PROCESS FOR PRODUCING AN AQUEOUS SUSPENSION OF NITRIFYING BACTERIA

[75] Inventor: Eberhard Bock, Hamburg, Fed. Rep. of Germany

[73] Assignee: TetraWerke Dr.rer.nat. U. Baensch GmbH, Herrenteich, Fed. Rep. of Germany

[21] Appl. No.: 249,913

[22] PCT Filed: Sep. 22, 1987

[86] PCT No.: PCT/EP87/00538
§ 371 Date: Jul. 25, 1988
§ 102(e) Date: Jul. 25, 1988

[87] PCT Pub. No.: WO88/02397
PCT Pub. Date: Apr. 7, 1988

[30] Foreign Application Priority Data

Sep. 25, 1986 [DE] Fed. Rep. of Germany ....... 3632532

[51] Int. Cl.$^4$ .............................................. C12N 1/20

[52] U.S. Cl. ............................. 435/253.6; 435/252.1; 435/300; 435/313

[58] Field of Search .................. 435/252.1, 253.6, 300, 435/313

[56] References Cited

U.S. PATENT DOCUMENTS

| 755,519 | 3/1904 | Moore | 435/252.1 |
| 865,965 | 9/1907 | Earp-Thomas | 435/252.1 |
| 4,072,577 | 2/1978 | Hurshaut | 435/253.6 |

Primary Examiner—Peter D. Rosenberg
Attorney, Agent, or Firm—Elizabeth M. Anderson

[57] ABSTRACT

The invention relates to a process for producing an aqueous suspension of nitrifying bacteria using a growth medium containing ammonia or nitrite, in which the bacteria remain metabolically and physiologically active by induction of the specific nitrification enzyme systems, in which the bacteria can be kept for long periods and can be finally used, as well as a device for carrying out the process.

15 Claims, 1 Drawing Sheet

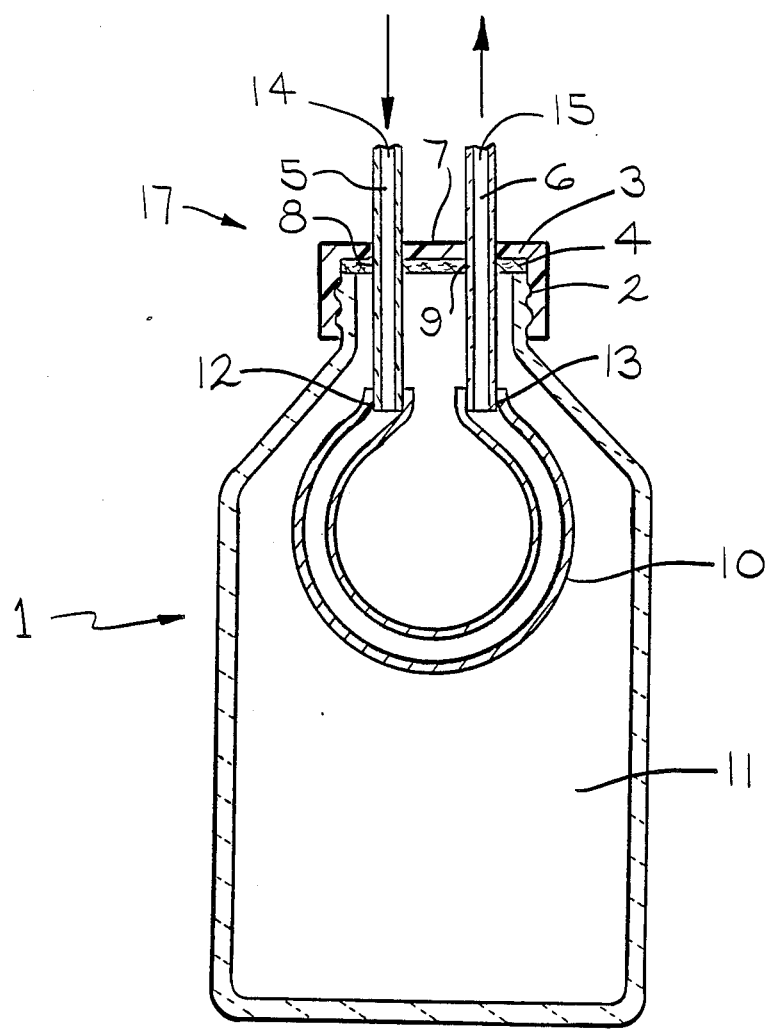

PROCESS FOR PRODUCING AN AQUEOUS SUSPENSION OF NITRIFYING BACTERIA

The invention relates to a process for producing an aqueous suspension of nitrifying bacteria using a growth medium containing ammonia or nitrite, in which the bacteria remain metabolically and physiologically active by induction of the specific nitrification enzyme systems, in which the bacteria can be kept for long periods and can be finally used, as well as a device for carrying out the process.

Like all viable organisms, bacteria are dependent on permanent energy supply at physiological temperatures. They derive the energy from the metabolization of different substances, whereby various metabolic groups have been created in evolution, specified according to the energy source, the hydrogen donor, and the carbon source. According to the hydrogen donor the organisms are designated as "organotroph" or "lithotroph". In the first case, organic compounds are used as energy source. On the other hand, lithotrophic growth is achieved when inorganic energy sources like $H_2$, $NH_3$, $H_2S$, $S$, $CO$, $Fe^{2+}$, $NH_4^+$ or $NO_2^-$ are used.

Between both metabolic types great differences exist, related to the generation time, when growth of organotrophically growing organisms like Pseudonomas or Escherichia is compared with growth of lithotrophic organisms like Nitrosomonas or Nitrobacter. Escherichia has generation times of approximately 20 min., whereas Nitrobacter has generation times of at least 10 h under lithotrophic conditions. The reason for that difference is the different amount of energy derived from the oxidation of substrates being utilized.

Due to the inorganic substrates used for energy generation, the metabolism of species of nitrifying bacteria is different. The oxidation of ammonia is performed in three steps, first the oxidation of ammonia to hydroxylamine by a monooxygenase.

(a) $NH_3 + XH_2 + O_2 \rightarrow NH_2OH + X + H_2O$

Subsequently, the oxidation of hydroxylamine is performed via nitroxyl to nitrite as the energy generating step. The key enzyme of this reaction is hydroxylamine oxidoreductase.

(b) $NH_2OH + 2\ Cyt\ c^{3+} (NOH) + 2\ H^+ + Cyt\ c^{2+}$
(c) $(NOH) + X + H_2O \rightarrow NO_2^- + XH_2 + H^+$ The bacterial nitrite oxidation can be summarized by the following equation

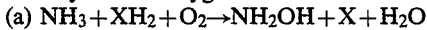
$NO_2 + 0,5\ O_2 \rightarrow NO_3-.$

However, the oxygen atom taken up from nitrite during oxydation does not originate from air, but from water. This is shown by the following partial reactions as well as the electrons released from nitrite and transfered to oxygen.

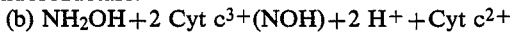
(a) $NO_2^- + H_2O + 2\ Cyt\ a_1^{3+} \rightarrow NO_3^- + 2\ H^+ + 2\ Cyt\ a_1^{2+}$
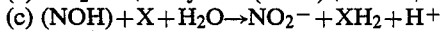
(b) $2\ Cyt\ a_1^{2+} + 2\ Cyt\ c^{3+} \rightarrow 2\ Cyt\ c^{2+} + 2\ Cyt\ a_1^{3+}$
(c) $2\ Cyt\ c^{2+} + 2\ Cyt\ aa_3^{3+} \rightarrow 2\ Cyt\ aa_3^{3+} + 2\ Cyt\ c^{3+}$
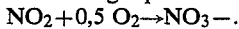
(d) $2\ Cyt\ aa_3^{2+} + 2\ H^+ + 0,5\ O_2 \rightarrow 2\ Cyt\ aa_3^{3+} + H_2O$ Membrane bound enzyme nitrite oxidoreductase is responsible for electron transfer to the respiratory chain. Another growth factor is the hydrogen ion concentration. Bacterial growth is dependent on the pH-value and has its optimum at pH 7,8. Higher as well as lower pH-values inhibit bit growth, and they are even toxic with greater deviations from the pH-optimum. Variations of pH-value may occur, when acid is produced by ammonia oxidation, or when organic acids supplied to the medium are metabolized and completely oxidized, resulting in an increase of the pH-value.

Oxygen supply is significant for bacterial growth. Aerobic organisms use molecular oxygen as terminal hydrogen acceptor, whereas anaerobically growing organisms use nitrate or sulfate for example as terminal hydrogen acceptor For the latter, oxygen is toxic even in low concentrations. However, high oxygen partial pressure may be toxic also for aerobic organisms. Furthermore, oxygen requirement changes with the growth phase. If the cells are in the logarithmic growth phase, their oxygen requirement is much higher than in the stationary phase. Resting cells need less oxygen than growing cells. Fast growing organisms like Escherichia coli and Pseudonomas can be grown at high cell concentrations without any problem by the method of a balanced aeration, when process controlled bioreaktors are used.

But so far, no methods exist to achieve such high cell concentrations with active cells of nitrifying bacteria.

Oxygen supply is also a problem when nitrifying bacteria are stored. To have high amounts of those cells available for industrial use, the cells must remain active and be protected against oxygen as well.

These complex relations between the necessary oxygen supply on the one hand and the anaerobic conditions on the other hand require a system for growing cells of different physiological states together.

The object of the invention is to provide a process for growing and storing nitrifying bacteria in an aqueous medium with induction of the specific nitrification enzyme systems to achieve high cell yield, e.g. for industrial use. The storage stability of nitrifying cells should be much higher than the storage stability of other bacteria like Escherichia coli or Pseudomonas, and even higher than the storage stability of nitrifying organisms grown according to common methods. Furthermore, the bacteria should remain active even after a storage period of e.g. one year or more.

According to the invention the problem of the process mentioned hereinbefore is solved according to the features of claim 1. Air, pure oxygen, or a mixture of air and pure oxygen is passed through a gas permeable non porous tube, arranged in loops and submerged in a suitable culture medium. As a result of positive aerotaxis, nitrifying bacteria adhere on the tube surface, forming a biofilm of extracellular polymers. The organisms grow in the region of the biofilm, which is produced only by nitrifiers. The oxygen consumption of an air carrying tube is so high that aerobic conditions only exist near the tube surface, which are in the region of the biofilm. Other zones of the medium are nearly anaerobic. There, the same organisms grow by reverting the nitrification, using organic compounds.

Generally, all facultatively chemolithoautotrophically growing nitrifying bacteria can be used to carry out the process according to the invention. Very high cell yields of more than 30 mg protein/l are achieved with members of the genus Nitrobacter (e.g. Nitrobacter winogradskyi ATCC 25 391, as well as with Nitrobacter hamburgensis, Arch. Microbiol. 136, 281-283).

According to a further feature of the invention, separate compartments can also be created by using culture flasks, like bottles, with a ratio of liquid surface to liquid volume being low, instead of using a gas carrying tube to grow nitrifying bacteria. If culture flasks are used with a sterile, but not gastight cap, a narrow zone of high oxygen partial pressure is created just below the liquid surface. A biofilm is formed on the liquid surface, which is similar in structure and composition to the biofilm on the tube. The cells nitrify in this zone and in the zone of high oxygen partial pressure just below, whereas cells are protected against oxygen in deeper zones, in which they grow anaerobically and remain in an active state for long periods. Common laboratory bottles (1) with a volume of 1 liter can be used, for example, to carry out the process. By closing the screw cap, the oxygen supply can be reduced easily that an oxygen diffusion rate is achieved, creating different compartments.

Of course, the correct growth medium is important. In the presence of organic compounds like yeast extract, peptone and pyruvate, and in the absence of oxygen, nitrifying bacteria use nitrate or nitrite, respectively, as terminal electron acceptor to generate growth energy. Such metabolism is achieved with 1.5 g yeast extract/l, 1.5 g peptone/l, 0.55 g pyruvate/l, and 2 g sodium nitrate/l. Even with only 0.15 g yeast extract/l, 0.15 g peptone/l, and 0.055 g pyruvate/l a nitrate reduction is achieved.

Other organic compounds, like glycerol, can also be used instead of pyruvate. Good growth is achieved with 1 g glycerol/l, whereby a cytotoxic increase of the pH-value does not occur from the oxidation of this substrate, compared to pyruvate or acetetate. Furthermore, it is not expensive to grow nitrifying bacteria in the presence of glycerol. The bacteria even grow with glycerol as the only organic substrate and with nitrate as electron acceptor.

To grow nitrifying organisms with a high nitrification activity, it is necessary to induce the enzyme nitrite oxidoreductase. The nitrite oxidation key enzyme is not only induced in the presence of nitrite, but also in presence of nitrate or under anaerobic conditions. The induction can be shown by biochemical analyses, e.g. estimation of enzyme activity or protein separation by polyacrylamide gel electrophoresis. Gel electrophoretic separations show a band pattern, typical for nitrifying Nitrobacter cells with major proteins of 32,000, 70,000, and 116,000 D.

Bacteria, grown according to the invention, can be used especially for industrial purpose. They can be used where nitrogen compounds like ammonia or nitrite must be eliminated. These compounds periodically contaminate the water for fish-hatching. The bacterial cultures can be used to eliminate these compounds in a natural way without pollution of the environment. Especially those bacterial strains can be developed, being naturally adapted to fresh or see water. Another field of application is the waste water and drinking water treatment. The bacteria grown according to the invention can be used as starting cultures to shorten long start phases.

Further features of the invention are described in the subclaimes and will be explained according to the culture flask shown in the drawing, used to carry out the process.

The invention covers a process for producing an aqueous suspension of nitrifying bacteria, in which the bacteria remain metabolically and physiologically active under induction of the specific nitrification enzyme systems, can be kept for long periods and can be finally used, using a growth medium containing ammonia a nitrite, characterized in that separate compartments having a higher or lower oxygen partial pressure are created in the sealed culture flask and that the bacterial culture is kept in the absence of oxygen at latest when the stationary growth phase has been reached.

The process is characterized in that a gas is passed through the suspension of nitrifying bacteria.

The process is further characterized in that the gas is passed through a tube membrane of non porous material, submerged in a suspension, which is kept in the absence of air.

The process is further characterized in that the gas passed through the tube membrane is air or oxygen.

The process is further characterized in that a continuous gas flow is passed through the tube membrane.

The process is for growing facultative chemolithoautotrophic organisms, characterized in that growth media are used containing a basal mineral salt medium, ammonia or nitrite or organic substrates.

The process is further characterized in that nitrite or nitrate is added to the basal medium as electron acceptor.

The process is further characterized in that glycerol, acetate, or pyruvate or combinations thereof are used as organic substrates.

The process is further characterized in that yeast extract and/or peptone are added to the growth medium.

The process is further characterized in that nitrifying bacteria are grown under aerobic conditions in an upper narrow zone of the medium, instead of using a tube submerged in the medium to create an aerob compartment beside an anaerob zone.

The process is further characterized in that a standing culture, which is neither shaked nor stirred and not gastight, has a liquid surface between gas phase and liquid phase of just the size that the rate for oxygen diffusion from the gas phase into the liquid phase is lower than the oxygen uptake rate in the medium for nitrifying bacteria.

The process is further characterized in that the bacteria are grown in the dark at a constant temperature of 30° C.

A device for carrying out the process of the invention is a culture flask with a closing device, characterized in that a gas permeable, non porous tube (10) arranged in loops is submerged in the growth medium (11) and connected at the end sections to a gas outlet tube (6).

The device is characterized in that gas inlet tube (5) and gas outlet tube (6) is arranged in holes (8, 9) of sealing (4) and connected to flask (1) together with tube (10) by means of closing device (17).

The device is characterized in that tube (10) consists of silicone rubber or the like.

The culture flask for bacteria is a flask 1 with a thread 2, which can be closed with a screw cap 3 and a sealing 4. Inlet tube 5 is arranged in holes 7, 8 of screw cap 3 and sealing 4, whereas outlet tube 6 is arranged in holes 7, 9. The ends 12, 13 of inlet and outlet tubes 5, 6 are connected to tube 10, which is arranged in loops and submerged in the growth medium 11. An air pump can be connected to inlet 14 of tube 5 used for gas supply. Outlet 15 opens the outlet tube 6 to the environment. To produce an aqueous suspension of nitrifying bacteria, flask 1 is filled with growth medium 11 up to the end 16 of thread 2, sterilized and subsequently inoculated with a bacterial culture. The inoculum used for nitrifying bacteria is 1–5%. The closing device 17 with inlet and outlet tubes 5, 6 as well as tube 10 is arranged and flask 1 is sealed by means of screw cap 3 and sealing 4. Gas, e.g. oxygen, is fed through inlet tube 5 and tube 10 to outlet tube 6 by means of an air pump or another gas supply device. The culture is incubated in the dark at 25–30° C., the optimum growth temperature for nitrifyiers. Samples can be taken periodically with a sterile cannula through the sealing 4 or after the closing device 17 has been taken off, to determine the growth phase. At latest when the stationary growth phase has been reached, oxygen supply is stopped. The whole closing device 17 with inlet and outlet tube 5, 6 and tube 10 can be exchanged for a common screw cap under sterile conditions. At this stage, cultures can be kept at 30° C. or at lower temperatures, e.g. at room temperature, for long periods.

I claim:

1. A process for producing an aqueous suspension of nitrifying bacteria, in which the bacteria remain metabolically and physiologically active under the induction of specific nitrification enzyme systems, can be kept for long periods in the absence of oxygen at a stationary growth phase and can be finally used, comprising a growth medium containing ammonia or nitrite, and separate compartments having a higher or lower oxygen partial pressure created in a sealed culture flask.

2. Process according to claim 1, characterized in that a gas is passed through the suspension of nitrifying bacteria.

3. Process according to claim 2, characterized in that the gas is passed through a tube membrane of non porours material, submerged in a suspension, which is kept in the absence of air.

4. Process according to claim 3, characterized in that the gas passed through the tube membrane is air or oxygen.

5. Process according to claim 4, characterized in that a continuous gas flow is passed through the tube membrane.

6. Process according to claims 1 for growing facultative chemolithoautotrophic organisms, characterized in that growth media are used containing a basal mineral salt medium, ammonia or nitrite or organic substrates.

7. Process according to claim 6, characterized in that nitrite or nitrate is added to the basal medium as electron acceptor.

8. Process according to claim 6, characterized in that glycerol, acetate, or pyruvate or combinations thereof are used as organic substrates.

9. Process according to claim 8, characterized in that yeast extract and/or peptone are added to the growth medium.

10. Process according to claim 3, characterized in that nitrifying bacteria are grown under aerobic conditions in an upper narrow zone of the medium, instead of using a tube submerged in the medium to create an aerob compartment beside an anaerob zone.

11. Process according to claim 10, characterized in that a standing culture, which is neither shaked nor stirred and not gastight, has a liquid surface between gas phase and liquid phase of just the size that the rate for oxygen diffusion from the gas phase into the liquid phase is lower than the oxygen uptake rate in the medium for nitrifying bacteria.

12. Process according to claim 11, characterized in that the bacteria are grown in the dark at a constant temperature of 30° C.

13. A device for carrying out the process according to claim 1 using a culture flask, with a closing device, characterized in that a gas permeable, nonporous tube (10) arranged in loops is a submerged in the growth medium (11) and connected at the end sections to a gas inlet tube (5) and a gas outlet tube (6).

14. Device according to claim 13, characterized in that gas inlet tube (5) and gas outlet tube (6) is arranged in holes (8, 9) of sealing (4) and connected to flask (1) together with tube (10) by means of closing device (17).

15. A device according to claim 13, characterized in that tube (10) consists of silicone rubber.

* * * * *